(12) United States Patent
Besch et al.

(10) Patent No.: US 8,998,895 B2
(45) Date of Patent: Apr. 7, 2015

(54) ELECTROSURGICAL INSTRUMENT AND METHOD FOR PRODUCING AN ELECTROSURGICAL INSTRUMENT

(75) Inventors: Hansjoerg Bjoern Besch, Gomaringen (DE); Britta Schwahn, Tuebingen (DE)

(73) Assignee: Erbe Elektromedizin GmbH, Tuebingen (DE)

(*) Notice: Subject to any disclaimer, the term of this patent is extended or adjusted under 35 U.S.C. 154(b) by 590 days.

(21) Appl. No.: 13/382,819

(22) PCT Filed: Jun. 16, 2010

(86) PCT No.: PCT/EP2010/003595
§ 371 (c)(1),
(2), (4) Date: Feb. 6, 2012

(87) PCT Pub. No.: WO2011/003503
PCT Pub. Date: Jan. 13, 2011

(65) Prior Publication Data
US 2012/0130364 A1 May 24, 2012

(30) Foreign Application Priority Data

Jul. 7, 2009 (DE) .......................... 10 2009 032 065
Oct. 5, 2009 (DE) .......................... 10 2009 048 312

(51) Int. Cl.
*A61B 18/18* (2006.01)
*A61N 1/06* (2006.01)
*A61B 18/14* (2006.01)
*A61B 18/00* (2006.01)
*A61B 18/02* (2006.01)

(52) U.S. Cl.
CPC .............. *A61N 1/06* (2013.01); *A61B 18/1477* (2013.01); *A61B 18/1492* (2013.01); *A61B 2018/00023* (2013.01); *A61B 2018/00047* (2013.01); *A61B 2018/00053* (2013.01); *A61B 2018/0231* (2013.01); *A61B 2018/0262* (2013.01); *A61B 2562/222* (2013.01)

(58) Field of Classification Search
USPC ....................................... 606/13–52
See application file for complete search history.

(56) References Cited

U.S. PATENT DOCUMENTS

| 5,697,927 | A | 12/1997 | Imran et al. |
| 5,957,884 | A * | 9/1999 | Hooven ........................ 604/48 |
| 2006/0217791 | A1 | 9/2006 | Spinka et al. |
| 2008/0154258 | A1 | 6/2008 | Chang et al. |

FOREIGN PATENT DOCUMENTS

| CN | 1512855 A | 7/2004 |
| CN | 101209217 A | 7/2008 |
| EP | 1 148 770 A2 | 10/2001 |
| EP | 1 902 683 A1 | 3/2008 |
| GB | 2 308 979 A | 7/1997 |
| WO | WO 01/41664 A1 | 6/2001 |

* cited by examiner

*Primary Examiner* — Scott Getzow
(74) *Attorney, Agent, or Firm* — Dickstein Shapiro LLP

(57) ABSTRACT

An electrosurgical instrument including a probe tube for transporting fluid, at least one electrode for devitalizing tissue, and at least one conducting foil electrical lead arranged along the longitudinal axis of the probe tube for providing a high frequency (RF) voltage at the electrode. A method of producing an electrosurgical instrument, including applying a conductive foil to a probe tube that extends along the longitudinal axis of the probe tube, and providing at least one electrode on the probe tube, wherein the electrode electrically connects to the conductive foil.

17 Claims, 1 Drawing Sheet

# ELECTROSURGICAL INSTRUMENT AND METHOD FOR PRODUCING AN ELECTROSURGICAL INSTRUMENT

CROSS-REFERENCE TO RELATED APPLICATIONS

This application claims priority to PCT/EP2010/003595, filed Jun. 16, 2010 and published as WO 2011/003503, which claims priority to DE102009032065.2, filed Jul. 7, 2009 and also to DE 102009048312.8, filed Oct. 5, 2009.

FIELD OF THE INVENTION

The disclosed embodiments relate to surgical instruments, and more particularly to electrosurgical instruments.

BACKGROUND OF THE INVENTION

In high-frequency (RF) surgery it is known to devitalize tissue in a targeted manner by means of the application of RF current. Such an operation can be performed with the use of a monopolar or bipolar instrument. With the use of a monopolar instrument, the current path usually leads from the electrosurgical instrument via the tissue to be treated to the neutral electrode. With the use of a bipolar instrument, the instrument is designed to have two sections that are electrically insulated from each other so the current path extends from a first section of the electrosurgical instrument via the tissue to be treated to a second section of the electrosurgical instrument.

Cryoprobes including distal and proximal electrodes for applying the appropriate current are known. These cryoprobes include a cooling device that allows cooling of the tissue that is in direct contact with the instrument. In doing so, it is possible to prevent any unwanted carbonization of the surrounding tissue, so that the instrument can be used for a controlled and potentially larger area devitalization. Furthermore, by using the cooling device in a targeted manner, the heat distribution can be controlled along the instrument, and thus the devitalization region can be adjusted.

Appropriate cooling can be accomplished, for example, by the targeted use of the Joule-Thomson effect. In this case, a fluid, in particular a gas, experiences a temperature change due to throttling (pressure change).

Electrosurgical instruments including a distal electrode and a proximal electrode provided on the outside of a probe tube are known.

A fluid or gas channel, within the lumen, can provide a cooling fluid to an expansion chamber at the distal end of the probe tube. The lumen of the probe tube is used to discharge the expanded fluid. To electrically connect the distal and the proximal electrodes with an RF generator, some electrodes may use a fluid or gas channel that is electrically conductive, and others may use a conductive lead that is separately arranged within the lumen and insulated relative to the gas channel. The electrical connection of the proximal electrode to the other conductive lead is difficult. Thus, openings are provided in the probe tube in order to provide appropriate electrical contact. The fluid transported in the lumen can then exit the lumen through these openings into the tissue and cause damage. Furthermore, the probes must have dimensions such that the lumen offers sufficient space for the accommodation of the additional lead. It is difficult to manufacture such probes while maintaining the small probe size necessary for minimally invasive procedures.

Publication EP 1 902 683 A1 has disclosed a catheter for the application of a current. To do so, the catheter comprises several electrodes that are supplied with a suitable voltage via the conductive path within a sheathing of the catheter. The conductive paths are located inside the exterior wall of the sheathing and are electrically insulated relative to each other.

BRIEF SUMMARY OF THE INVENTION

The disclosed embodiments relate to an electrosurgical instrument as well as to a method for producing an electrosurgical instrument. It is the object of the disclosed embodiments to provide an electrosurgical device that is safe, has suitable dimensions, and is easily and efficiently manufactured.

In one embodiment, the electrosurgical instrument includes a probe tube for transporting fluid, as well as at least one electrode, in particular a distal electrode and/or a proximal electrode, for devitalizing tissue. The electrosurgical instrument includes at least one electrical lead for providing an RF voltage to the electrode. The electrical lead may be a conductive foil arranged along a longitudinal axis of the probe tube.

It is a particular advantage of the disclosed embodiments that an electrically conductive exterior skin, i.e., the conductive foil of the probe tube, is used as the electrical conductor or as the conductor path. Consequently, the electrical lead can be provided for at least one electrode, preferably for the proximal electrode, without requiring the electrical lead be taken into consideration when dimensioning the probe tube. Providing the conductive foil results in only a minimal additional increase of the wall thickness, so that relatively small probes can be developed. Compared with the prior art, it is not necessary to perforate the probe tube in order to produce an appropriate electrical pathway. Therefore, the process of manufacturing an electrosurgical instrument in accordance with the invention is also relatively simple.

The transported fluid may be a gas, a fluid, or a gas/fluid mixture. The conductive foil may be a copper foil, gold foil or silver foil. Copper foil, gold foil, or silver foil may be understood to include any suitable foil of a copper alloy, gold alloy, or silver alloy respectively. By using the copper foil it is possible to produce a suitable conductor displaying minimal wall thickness. Also, copper exhibits a low specific resistance.

The conductive foil may be arranged in a helical structure along the probe tube. This helical winding of the foil allows the necessary flexibility of the instrument, in particular the probe tube, to be only minimally affected. This ensures that the electrosurgical instrument remains sufficiently navigable, so that it can be moved without problems inside the working channel of an endoscope. Indeed, it would be theoretically conceivable to arrange the conductive foils on one side in the form of a direct conductor path along the longitudinal direction of the probe tube or to provide a zigzag foil track on one side of the probe tube. However, this would also cause a one-sided change of the flexibility and/or elasticity of the tube. This would have a negative effect on navigability.

Theoretically, the individual adjacent tracks of the conductive foil could be arranged so as to overlap—at least in sections—along the longitudinal direction of the probe tube. Consequently, an essentially tubular conductive path would be formed that only minimally affects the flexibility of the probe tube and exhibits only a minimal inductive resistance. Preferably, the adjacent tracks of conductive foil are arranged in longitudinal direction of the probe tube at a distance from each other so that no overlapping occurs. Any overlapping represents an additional thickening of the diameter of the electrosurgical instrument. Due to the width of the tracks of the conductive foil, the inductive resistance is tolerable.

The instrument may include an insulator layer that covers—at least in sections—the conductive foil in order to fixate the foil. Preferably, the resultant cross-section shows an arrangement that is configured from the inside of the probe tube toward the outside as follows: wall of the probe tube, conductive foil, insulator layer. The insulator layer may be extremely thin-walled and insulates the conductor path formed by the conductive foil against the outside region. Furthermore, the insulator protects the conductive foil against outside influences and is able to hold the conductive foil in place. The insulator layer may be produced of a material that only minimally affects the flexibility of the probe tube and thus the electrosurgical instrument.

At least one electrode, preferably the proximal electrode, is able to directly contact the conductive foil. Consequently, the electrical connection between the conductive foil and the associated electrode may be designed in the easiest possible way. Soldering at this site is not necessary. Consequently the connecting technique is strictly space-appropriate. By means of a mechanical connecting technique, it is also possible to establish appropriate connections in the proximal region of the probe tube. For example, contacting may be accomplished by crimping.

The electrosurgical instrument may be a cryoprobe comprising a fluid channel for a cooling fluid (e.g., a gas channel). In one embodiment, the fluid channel is an electrical conductor and is connected with the at least one electrode to provide the RF voltage. The electrosurgical instrument may be a cryoprobe that preferably includes a gas channel extending within a lumen of the probe tube. The fluid introduced through the fluid channel may be discharged from a distal region of the probe via the lumen. Preferably, the fluid channel is fabricated—at least in sections—of an electrically conductive material and thus also acts as a conductor path. This conductor path can be used to connect another electrode, preferably the distal electrode, with the RF generator.

The disclosed embodiments also include a method for producing an electrosurgical instrument. The method includes applying a conductive foil to a probe tube including a first end and a second end defining a longitudinal axis between the first and second ends, wherein the conductive foil extends along the longitudinal axis of the probe tube. The method may further include providing a first electrode on the second end of the probe tube, wherein the first electrode electrically connects to the conductive foil. In one embodiment the method further includes providing at least one connection on the first end of the probe tube.

DETAILED DESCRIPTION OF THE INVENTION

In the description hereinafter, the same reference signs will be used for parts that are the same or that have the same function.

Figure 1:
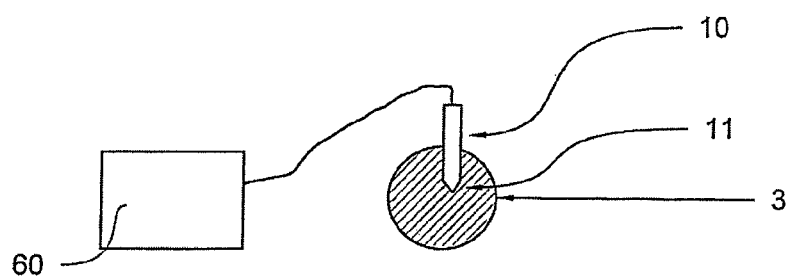
FIG. 1 is a schematic representation of an electrosurgical device in accordance with a disclosed embodiment.

FIG. 1 shows an RF surgical device for devitalizing tissue. An ablation probe 10 is connected via a supply tube and several cables with a supply device 60. The ablation probe 10 is inserted into a tissue 3 that is to be devitalized by means of an RF current, the current being applied through the ablation probe. For this, electrodes, i.e., a distal electrode 30 and a proximal electrode 35, shown in FIG. 2, arranged on the ablation probe 10 are connected with an RF generator in the supply unit 60. In order to completely devitalize the tissue 3, it is necessary to cool the ablation probe 10 in at least some sections in order to avoid a carbonization of the tissue contacted by the ablation probe 10. Therefore, the ablation probe 10, in accordance with an embodiment of the invention, comprises a cooling system that is fed by the supply unit 60.

FIG. 1 is a schematic representation of the use of the ablation probe 10. In fact, such probes are frequently moved toward the target tissue by means of endoscopes in order to perform a minimally invasive procedure. To do so, it is necessary to keep the diameter of the ablation probe 10 as small as possible. Furthermore, the ablation probe 10 must be flexible in order to be able to perform a devitalization at sites that are only accessible with difficulty. Regarding flexibility, it should also be noted that probes that can be more readily bent in one direction than in another are frequently perceived by the treating physician as being unsuitable, because it is difficult to guide such ablation probes 10 in the working channel.

Figure 2:
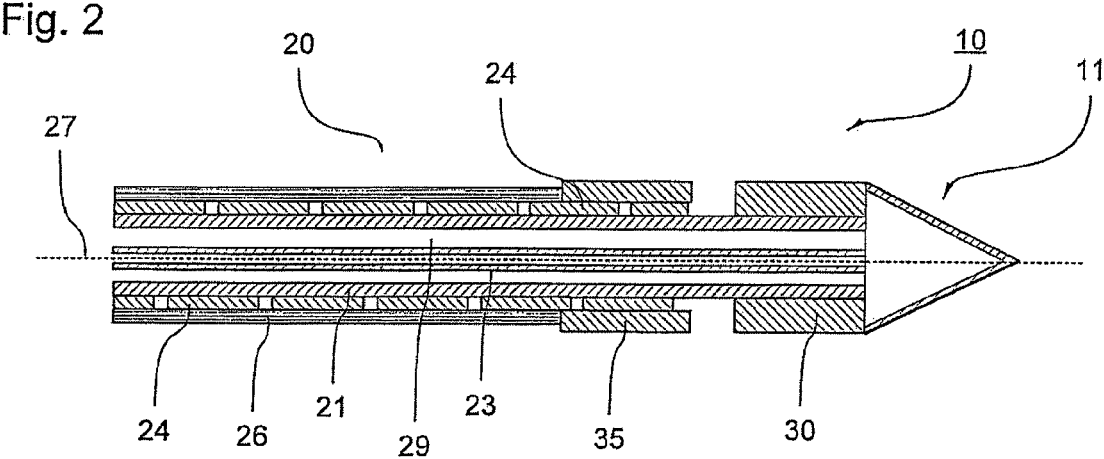
FIG. 2 is a sectional view through the ablation probe in accordance with FIG. 1.

FIG. 2 shows one embodiment of the ablation probe 10 including a probe tube 21 with a proximal end and a distal end. A probe tip 11 is provided on the distal end of the probe tube 21, the probe tip 11 terminating the ablation probe 10. A handle for guiding the ablation probe 10 and connections for connecting the ablation probe 10 with the supply unit 60 can be provided on the proximal end of the probe tube 21.

The probe tube 21 defines a theoretical longitudinal axis 27 of the ablation probe 10, the axis extending from the proximal end to the distal end of the ablation probe 10. Inside the probe tube 21 (i.e., within lumen 29), there is a flexible gas channel 23 that extends from the proximal end of the ablation tube 10 to the probe tip 11. A fluid, preferably $N_2O$, is introduced into the ablation probe 10 via this gas channel 23. The fluid expands at a distal end of the gas channel and removes thermal energy from the ablation probe 10, thereby cooling the ablation probe 10. The expanded fluid is discharged via the lumen 29 and discarded. Consequently, the probe tube 21, the gas channel 23, and the probe tip 11 (acting as the expansion chamber) represent part of the cooling system of the ablation probe 10.

Continuing with FIG. 2, the distal electrode 30 that encloses the probe tube 21 in a ring-like manner is located in the immediate vicinity of the probe tip 11 on the distal end of the probe tube 21. Although not shown in FIG. 2, the distal electrode 30 is in electrical contact with the gas channel 23 that is made of an electrically conductive material. Consequently, the gas channel 23 represents at least a part of a first conductor path for supplying the distal electrode 30. In one embodiment, the distal electrode 30 can be in direct contact with the preferably electrically conductive probe tip 11, thereby being a part thereof.

In one embodiment, a second conductor path or electrical lead for supplying the proximal electrode 35 is made of a copper foil 24. The proximal electrode 35 is also an annular electrode that encloses the probe tube 21 and is preferably arranged coaxially with respect to the longitudinal axis 27. The proximal electrode 35 is offset relative to the distal electrode 30 in the proximal direction and provided at a distance from the distal electrode 30 that is sufficient to provide an electrically insulating gap. This gap can be filled with an insulator.

The copper foil 24 is directly applied to the probe tube 21 and is configured as a helix-like coil, whereby the copper foil 24 extends from the proximal end of the probe tube to below the proximal electrode 35. The individual coils around the probe tube 21 are referred to as tracks, wherein, in the shown exemplary embodiment, the individual tracks are at essentially the same distance from each other in the longitudinal direction. Theoretically, it would be possible to vary the distances of the individual tracks from each other. The helical structure or the helix-like arrangement of the copper foil 24 displays a constant pitch. The proximal electrode 35 is directly applied to the copper foil 24 and thus contacts said copper foil. The electrical contact between the copper foil 24 and the proximal electrode 35 is thus ensured.

Preferably, the ablation probe 10 comprises an exterior insulation 26 that is applied to the copper foil 24. This exterior insulation 26 extends from the proximal end of the ablation probe 10 to the proximal electrode 35. The electrical contact of the copper foil 24 with the proximal end can be achieved by crimping.

The probe tube 21, the copper foil 24, the exterior insulation 26, the distal electrode 30 and the proximal electrode 35 form a probe body 20.

The helical structure of the copper foil 24 is a ribbon that winds along the probe tube 21 at a constant pitch. The coils, as well as the exterior insulation 27, may be configured in such a manner that they increase the stability of the ablation probe 10 while retaining a necessary flexibility.

The described contact between the copper foil 24 and the proximal electrode 35 can also be achieved in a simple manner from the viewpoint of the manufacturing process. This suggested electrical connection increases safety. Because the conductor or the conductor track is provided on the outside of the probe tube 21, it is not necessary to provide any passages or bores through the probe tube 21. The gas tightness of the probe tube 21 remains maintained.

It should be clear that, instead of the described one copper foil 24, it is possible to arrange several copper foils parallel to each other in order to contact several electrodes that are electrically insulated from each other. For example, the distal electrode 30 and the proximal electrode 35 could be supplied via corresponding copper foils 24. In this case, the electrically conductive gas channel 23 could be omitted. It should also be obvious to the person skilled in the art that another embodiment can also be reasonably employed in monopolar instruments.

In an exemplarily embodiment, the tracks of the copper foil 24 are arranged parallel to each other. Thus, there is no overlapping of the copper foil 24. Due to the narrow distance of the coils from each other and the width of the copper foil 24, the copper foil 24 almost acts like a pipeline, and the respective resistances are minimal. However, it would also be possible to arrange the copper foil 24 in an overlapping manner in order to reduce the inductive resistance.

The ablation probe 10 of FIG. 2 comprises two annular electrodes that enclose the probe tube 21. According to another embodiment, however, it is also possible to provide any other electrodes along the probe body 20 of the ablation probe 10. For example, the annular electrodes could be interrupted in sections or be replaced by plate electrodes that extend along the longitudinal axis 27, for example.

Although, an ablation electrode 10 was described, wherein a gas is transported through a gas channel 23 into the distal region of the ablation probe 10 for expansion, the present invention is not restricted to this specific embodiment. The invention can be used with any type of tubes, whether such tubes are used for transporting a gas, a fluid, or an analogical mixture.

The invention claimed is:

1. An electrosurgical instrument comprising:
   a probe tube having a longitudinal axis for transporting fluid;
   at least one electrode for devitalizing tissue; and
   at least one electrical lead for providing an RF voltage to the electrode,
   wherein the electrical lead comprises a conductive foil arranged along the longitudinal axis of the probe tube, and
   wherein the conductive foil is arranged in a helical structure around the probe tube along the longitudinal axis of the probe tube.

2. The electrosurgical instrument of claim 1, wherein the at least one electrode comprises a distal electrode and/or a proximal electrode.

3. The electrosurgical instrument of claim 1, wherein the conductive foil is a material selected from the group consisting of gold, silver, copper, or alloy thereof.

4. The electrosurgical instrument of claim 1, wherein the conductive foil is a copper foil.

5. The electrosurgical instrument of claim 1, wherein adjacent tracks of the helical structure are spaced apart from each other in the longitudinal direction of the probe tube.

6. The electrosurgical instrument of claim 1, further comprising an insulator layer that covers at least part of the conductive foil.

7. The electrosurgical instrument of claim 1, wherein the at least one electrode is in electrical contact with the conductive foil.

8. The electrosurgical instrument of claim 5, wherein the at least one electrode is in direct contact with the conductive foil.

9. The electrosurgical instrument of claim 1, wherein the electrosurgical instrument is a cryoprobe further comprising a fluid channel, wherein the fluid channel is an electrical conductor and is electrically connected with at least one electrode.

10. The electrosurgical instrument of claim 9, wherein the fluid channel is electrically connected to a first electrode and the conductive foil is electrically connected to a second electrode different than the first electrode.

11. The electrosurgical instrument of claim 9, wherein the probe tube defines a lumen and the fluid channel is arranged in the lumen of the probe tube.

12. A method of manufacturing an electrosurgical instrument, the method comprising:
   applying a conductive foil to a probe tube, the probe tube defining a longitudinal axis, wherein the conductive foil extends along the longitudinal axis of the probe tube;
   providing a first electrode on the probe tube, wherein the first electrode is electrically connected to the conductive foil; and
   providing at least one connection on a proximal first end of the probe tube, the at least one connection providing electrical connection to the conductive foil,
   wherein the conductive foil is arranged in a helical structure around the probe tube along the longitudinal axis of the probe tube.

13. The method of claim 12, wherein the conductive foil is a material selected from the group consisting of gold, silver, copper, or alloy thereof.

14. The method of claim 12, wherein the conductive foil is a copper foil.

15. The method of claim 12, wherein adjacent tracks of the helical structure are spaced apart from each other in the longitudinal direction of the probe tube.

16. The method of claim 12, further comprising an insulator layer that covers at least part of the conductive foil.

17. The method of claim 12, further comprising:
provproviding a second electrode on the probe tube, the second electrode being positioned distally to the first electrode;
providing a fluid channel inside the probe tube, wherein the fluid channel provides cooling to the distal end of the probe tube, wherein the fluid channel comprises regions of electrical conductivity; and
establishing an electrical connection between the second electrode and the fluid channel.

\* \* \* \* \*